(12) United States Patent
Sampson et al.

(10) Patent No.: US 7,674,260 B2
(45) Date of Patent: Mar. 9, 2010

(54) EMERGENCY HEMOSTASIS DEVICE UTILIZING ENERGY

(75) Inventors: Russel M. Sampson, Palo Alto, CA (US); Eugene V. Skalnyi, Los Altos, CA (US)

(73) Assignee: Cytyc Corporation, Marlborough, MA (US)

( * ) Notice: Subject to any disclaimer, the term of this patent is extended or adjusted under 35 U.S.C. 154(b) by 579 days.

(21) Appl. No.: 11/118,653

(22) Filed: Apr. 28, 2005

(65) Prior Publication Data

US 2006/0247614 A1 Nov. 2, 2006

(51) Int. Cl.
*A61B 18/14* (2006.01)

(52) U.S. Cl. .............................. 606/41; 606/48; 606/50; 607/150

(58) Field of Classification Search .................... 606/41; 607/101
See application file for complete search history.

(56) References Cited

U.S. PATENT DOCUMENTS

| | | | |
|---|---|---|---|
| 552,832 | A | 1/1896 | Fort |
| 725,731 | A | 4/1903 | Linn |
| 1,620,929 | A | 3/1927 | Wallerich |
| 1,827,306 | A | 10/1931 | Chapman et al. |
| 2,190,383 | A | 2/1940 | Newman |
| 2,347,195 | A | 4/1944 | Huff |
| 2,466,042 | A | 4/1949 | Reich et al. |
| 3,228,398 | A | 1/1966 | Leonard et al. |
| 3,324,855 | A | 6/1967 | Heimlich |
| 3,645,265 | A | 2/1972 | Majzlin |
| 3,840,016 | A | 10/1974 | Lindemann |
| 3,845,771 | A | 11/1974 | Vise |
| 3,858,586 | A | 1/1975 | Lessen |
| 3,877,464 | A | 4/1975 | Vermes |
| 3,924,628 | A | 12/1975 | Droegemueller et al. |
| 3,948,270 | A | 4/1976 | Hasson |
| 3,967,625 | A | 7/1976 | Yoon |
| 3,971,378 | A | 7/1976 | Krantz |
| 4,022,215 | A | 5/1977 | Benson |
| 4,057,063 | A | 11/1977 | Gieles et al. |

(Continued)

FOREIGN PATENT DOCUMENTS

DE 384246 10/1923

(Continued)

OTHER PUBLICATIONS

Patent Corporation Treaty PCT International Search Report, PCT Application Serial No. PCT/US2006/014898, Nov. 10, 2006, 5 pp.

(Continued)

*Primary Examiner*—Lee S Cohen
(74) *Attorney, Agent, or Firm*—Marc A. Vivenzio; Lindsay McGuiness

(57) ABSTRACT

A method and system for achieving hemostasis (the stoppage of bleeding) is described. RF (radio frequency) energy is used to ablate the surface of tissue to stop bleeding. The depth of destruction of the tissue can be controlled so as to desiccate and coagulate the tissue. In one implementation, an electrode carrier including bipolar electrodes is applied to the tissue, and RF energy transmitted through the bipolar electrodes to ablate the tissue. A layer of desiccated tissue can be created as well as coagulation of the tissue to achieve hemostasis.

25 Claims, 9 Drawing Sheets

U.S. PATENT DOCUMENTS

| | | |
|---|---|---|
| 4,082,096 A | 4/1978 | Benson |
| 4,158,050 A | 6/1979 | Zipper |
| 4,185,618 A | 1/1980 | Corey |
| 4,233,025 A | 11/1980 | Larson et al. |
| 4,359,454 A | 11/1982 | Hoffman |
| 4,380,238 A | 4/1983 | Colucci et al. |
| 4,415,288 A | 11/1983 | Gordon et al. |
| 4,449,528 A | 5/1984 | Auth et al. |
| 4,465,072 A | 8/1984 | Taheri |
| 4,492,231 A | 1/1985 | Auth |
| 4,532,924 A | 8/1985 | Auth et al. |
| 4,568,326 A | 2/1986 | Rangaswamy |
| 4,582,057 A | 4/1986 | Auth et al. |
| 4,601,698 A | 7/1986 | Moulding, Jr. |
| 4,606,336 A | 8/1986 | Zeluff |
| 4,628,924 A | 12/1986 | Cimber |
| 4,662,383 A | 5/1987 | Sogawa et al. |
| 4,676,258 A | 6/1987 | Inokuchi et al. |
| 4,691,703 A | 9/1987 | Auth et al. |
| 4,765,331 A | 8/1988 | Petruzzi et al. |
| 4,788,966 A | 12/1988 | Yoon |
| 4,832,048 A | 5/1989 | Cohen |
| 4,865,047 A | 9/1989 | Chou et al. |
| 4,869,268 A | 9/1989 | Yoon |
| 4,946,440 A | 8/1990 | Hall |
| 4,949,718 A | 8/1990 | Neuwirth et al. |
| 4,955,377 A | 9/1990 | Lennox et al. |
| 4,960,133 A | 10/1990 | Hewson |
| 4,961,435 A | 10/1990 | Kitagawa et al. |
| 4,979,948 A | 12/1990 | Geddes et al. |
| 4,981,465 A | 1/1991 | Ballan et al. |
| 4,983,177 A | 1/1991 | Wolf |
| 5,026,379 A | 6/1991 | Yoon |
| 5,047,028 A | 9/1991 | Qian |
| 5,057,106 A | 10/1991 | Kasevich et al. |
| 5,065,751 A | 11/1991 | Wolf |
| 5,078,717 A | 1/1992 | Parins et al. |
| 5,084,044 A | 1/1992 | Quint |
| 5,105,808 A | 4/1992 | Neuwirth et al. |
| 5,147,353 A | 9/1992 | Everett |
| 5,159,925 A | 11/1992 | Neuwirth et al. |
| 5,186,181 A | 2/1993 | Franconi et al. |
| 5,188,122 A | 2/1993 | Phipps et al. |
| 5,188,602 A | 2/1993 | Nichols |
| 5,217,473 A | 6/1993 | Yoon |
| 5,226,908 A | 7/1993 | Yoon |
| 5,242,437 A | 9/1993 | Everett et al. |
| 5,248,312 A | 9/1993 | Langberg |
| 5,263,585 A | 11/1993 | Lawhon et al. |
| 5,277,201 A | 1/1994 | Stern |
| 5,308,327 A | 5/1994 | Heaven et al. |
| 5,318,532 A | 6/1994 | Frassica |
| 5,322,507 A | 6/1994 | Costello et al. |
| 5,334,193 A | 8/1994 | Nardella |
| 5,334,209 A | 8/1994 | Yoon |
| 5,354,295 A | 10/1994 | Guglielmi et al. |
| 5,364,393 A | 11/1994 | Auth et al. |
| 5,370,649 A | 12/1994 | Gardetto et al. |
| 5,374,261 A | 12/1994 | Yoon |
| 5,374,283 A | 12/1994 | Flick |
| 5,380,317 A | 1/1995 | Everett et al. |
| 5,383,917 A | 1/1995 | Desai et al. |
| 5,395,311 A | 3/1995 | Andrews |
| 5,405,322 A | 4/1995 | Lennox et al. |
| 5,407,071 A | 4/1995 | Lawhon et al. |
| 5,433,708 A | 7/1995 | Nichols et al. |
| 5,437,629 A | 8/1995 | Goldrath |
| 5,443,470 A | 8/1995 | Stern et al. |
| 5,451,204 A | 9/1995 | Yoon |
| 5,474,089 A | 12/1995 | Waynant |
| 5,505,730 A | 4/1996 | Edwards |
| 5,507,743 A | 4/1996 | Edwards et al. |
| 5,514,091 A | 5/1996 | Yoon |
| 5,562,703 A | 10/1996 | Desai |
| 5,562,720 A | 10/1996 | Stern et al. |
| 5,588,961 A | 12/1996 | Leone et al. |
| 5,593,404 A | 1/1997 | Costello et al. |
| 5,609,598 A | 3/1997 | Laufer et al. |
| 5,613,950 A | 3/1997 | Yoon |
| 5,649,924 A | 7/1997 | Everett et al. |
| 5,656,013 A | 8/1997 | Yoon |
| 5,667,520 A | 9/1997 | Bonutti |
| 5,697,882 A | 12/1997 | Eggers et al. |
| 5,702,438 A | 12/1997 | Avitall |
| 5,716,343 A | 2/1998 | Kriesel et al. |
| 5,730,136 A | 3/1998 | Laufer et al. |
| 5,730,725 A | 3/1998 | Yoon |
| 5,769,880 A | 6/1998 | Truckai et al. |
| 5,779,698 A | 7/1998 | Clayman et al. |
| 5,797,903 A | 8/1998 | Swanson et al. |
| 5,800,482 A | 9/1998 | Pomeranz et al. |
| 5,807,389 A | 9/1998 | Gardetto et al. |
| 5,810,847 A | 9/1998 | Laufer et al. |
| 5,827,273 A | 10/1998 | Edwards |
| 5,843,121 A | 12/1998 | Yoon |
| 5,846,238 A | 12/1998 | Jackson et al. |
| 5,871,469 A | 2/1999 | Eggers et al. |
| 5,879,348 A | 3/1999 | Owens et al. |
| 5,885,601 A | 3/1999 | Sokal |
| 5,888,198 A | 3/1999 | Eggers et al. |
| 5,891,134 A | 4/1999 | Goble et al. |
| 5,891,136 A | 4/1999 | McGee et al. |
| 5,897,551 A | 4/1999 | Everett et al. |
| 5,897,553 A | 4/1999 | Mulier et al. |
| 5,935,137 A | 8/1999 | Saadat et al. |
| 5,938,660 A | 8/1999 | Swartz et al. |
| 5,954,715 A | 9/1999 | Harrington et al. |
| 5,954,717 A | 9/1999 | Behl et al. |
| 6,002,968 A | 12/1999 | Edwards |
| 6,014,589 A | 1/2000 | Farley et al. |
| 6,033,397 A | 3/2000 | Laufer et al. |
| 6,036,687 A | 3/2000 | Laufer et al. |
| 6,041,260 A | 3/2000 | Stern et al. |
| 6,042,596 A | 3/2000 | Bonutti |
| 6,068,613 A | 5/2000 | Kriesel et al. |
| 6,068,626 A | 5/2000 | Harrington et al. |
| 6,071,277 A | 6/2000 | Farley et al. |
| 6,077,257 A | 6/2000 | Edwards et al. |
| 6,096,052 A | 8/2000 | Callister et al. |
| 6,117,101 A | 9/2000 | Diederich et al. |
| 6,123,702 A | 9/2000 | Swanson et al. |
| 6,135,997 A | 10/2000 | Laufer et al. |
| 6,139,527 A | 10/2000 | Laufer et al. |
| 6,152,899 A | 11/2000 | Farley et al. |
| 6,159,207 A | 12/2000 | Yoon |
| 6,164,280 A | 12/2000 | Everett et al. |
| 6,165,172 A | 12/2000 | Farley et al. |
| 6,179,832 B1 | 1/2001 | Jones et al. |
| 6,183,468 B1 | 2/2001 | Swanson |
| 6,200,312 B1 | 3/2001 | Zikorus et al. |
| 6,231,496 B1 | 5/2001 | Wilk et al. |
| 6,231,507 B1 | 5/2001 | Zikorus et al. |
| 6,234,178 B1 | 5/2001 | Goble |
| 6,237,606 B1 | 5/2001 | Zikorus et al. |
| 6,238,393 B1 | 5/2001 | Mulier et al. |
| 6,245,065 B1 | 6/2001 | Panescu et al. |
| 6,245,090 B1 | 6/2001 | Gilson et al. |
| 6,258,084 B1 | 7/2001 | Goldman et al. |
| 6,263,248 B1 | 7/2001 | Farley et al. |
| 6,277,089 B1 | 8/2001 | Yoon |
| 6,293,942 B1 | 9/2001 | Goble et al. |
| 6,296,639 B1 | 10/2001 | Truckai et al. |
| 6,309,384 B1 | 10/2001 | Harrington et al. |
| 6,315,776 B1 | 11/2001 | Edwards et al. |

| | | | |
|---|---|---|---|
| 6,322,559 B1 | 11/2001 | Daulton et al. | |
| 6,346,102 B1 | 2/2002 | Harrington et al. | |
| 6,352,549 B1 | 3/2002 | Everett | |
| 6,364,877 B1 | 4/2002 | Goble et al. | |
| 6,369,465 B1 | 4/2002 | Swanson | |
| 6,395,012 B1 | 5/2002 | Yoon et al. | |
| 6,398,780 B1 | 6/2002 | Farley et al. | |
| 6,428,537 B1 | 8/2002 | Swanson | |
| 6,432,116 B1 | 8/2002 | Callister et al. | |
| 6,475,213 B1 | 11/2002 | Whayne et al. | |
| 6,485,500 B1 | 11/2002 | Kokish et al. | |
| 6,508,815 B1 | 1/2003 | Strul et al. | |
| 6,554,780 B1 | 4/2003 | Sampson et al. | |
| 6,584,359 B1 * | 6/2003 | Motoi | 607/76 |
| 6,663,626 B2 | 12/2003 | Truckai et al. | |
| 6,679,269 B2 | 1/2004 | Swanson | |
| 6,712,810 B2 | 3/2004 | Harrington et al. | |
| 6,712,815 B2 | 3/2004 | Sampson et al. | |
| 6,726,682 B2 | 4/2004 | Harrington et al. | |
| 6,743,184 B2 | 6/2004 | Sampson et al. | |
| 6,813,520 B2 | 11/2004 | Truckai et al. | |
| 2001/0041900 A1 | 11/2001 | Callister et al. | |
| 2002/0022870 A1 | 2/2002 | Truckai et al. | |
| 2002/0029051 A1 | 3/2002 | Callister et al. | |
| 2002/0072499 A1 | 6/2002 | Clagett | |
| 2002/0072745 A1 | 6/2002 | Truckai et al. | |
| 2003/0093101 A1 | 5/2003 | O'Heeron et al. | |
| 2003/0130711 A1 | 7/2003 | Pearson | |
| 2003/0199863 A1 | 10/2003 | Swanson | |
| 2004/0054368 A1 | 3/2004 | Truckai et al. | |
| 2004/0118166 A1 | 6/2004 | Huang et al. | |
| 2004/0172051 A1 | 9/2004 | Ravikumar | |
| 2004/0204720 A1 | 10/2004 | Harrington et al. | |
| 2004/0255958 A1 | 12/2004 | Harrington et al. | |
| 2005/0085880 A1 | 4/2005 | Truckai et al. | |
| 2005/0217680 A1 | 10/2005 | Callister et al. | |
| 2006/0206109 A1 * | 9/2006 | Swanson | 606/41 |

FOREIGN PATENT DOCUMENTS

| | | |
|---|---|---|
| DE | 22 22 820 | 11/1973 |
| DE | 4001086 | 1/1990 |
| EP | 0 056 178 A1 | 4/1981 |
| EP | 0 584 930 A1 | 7/1993 |
| EP | 1 400 182 | 6/2004 |
| FR | 774.550 | 9/1934 |
| FR | 70.43012 | 6/1972 |
| JP | 48-67586 | 9/1973 |
| JP | 58-32756 | 2/1983 |
| JP | 63-318934 | 12/1988 |
| WO | WO 92/19145 | 11/1992 |
| WO | WO 94/00178 | 1/1994 |
| WO | WO 94/07445 | 4/1994 |
| WO | WO 94/10948 | 5/1994 |
| WO | WO 94/23794 | 10/1994 |
| WO | WO 95/04385 | 2/1995 |
| WO | WO 95/05869 | 3/1995 |
| WO | WO 95/07664 | 3/1995 |
| WO | WO 95/10326 | 4/1995 |
| WO | WO 99/58070 | 11/1999 |
| WO | WO 01/97897 | 12/2001 |

OTHER PUBLICATIONS

D.E. Haines et al., "Observations on Electrode-Tissue Interface Temperature and Effect on Electrical Impedance During Radiofrequency Ablation of Ventricular Myocardium," *Circulation*, vol. 82, No. 3, Sep. 1990, pp. 1034-1038.

C. Nibley et al., "Prevention of Impedance Rise During Radiofrequency Current Catheter Ablation by Intra-Electrode Tip Chilling," *Circulation* [Abstracts From the 67th Scientific Sessions, Dallas Convention Center, Dallas, Texas, Nov. 14-17, 1994], vol. 90, No. 4, Part 2, Oct. 1994, p. 460.

W.M. Jackman et al., "Radiofrequency Current Directed Across the Mitral Anulus With a Bipolar Epicardial-Endocardial Catheter Electrode Configuration in Dogs," *Circulation*, vol. 78, No. 5, Nov. 1988, pp. 1288-1298.

* cited by examiner

EMERGENCY HEMOSTASIS DEVICE UTILIZING ENERGY

TECHNICAL FIELD

This invention relates to a medical device and procedure.

BACKGROUND

A trauma victim with a wound to certain organs in the body can be at significant risk of bleeding to death if the bleeding cannot be quickly controlled. For example, the liver is formed from a parenchymatous (porous) tissue that can bleed profusely when injured. A conventional technique for controlling the bleeding is to apply immediate pressure to the tissue, however, as soon as the pressure is removed, the bleeding can resume. Gauze type products, such as QuikClot® are available, that include a hemostatic agent to promote blood clotting. However, when applied to an organ like the liver, removing the gauze can reopen the wound, leading to additional bleeding. To prevent a trauma victim from bleeding to death, bleeding must be stopped immediately and often cannot wait until a victim is transferred to a medical facility.

SUMMARY

This invention relates to a medical device and procedure. In general, in one aspect, the invention features an apparatus for substantially achieving hemostasis by tissue ablation. The apparatus includes a base member, an electrode carrier, a vacuum line and a controller. The electrode carrier is attached to a surface of the base member and includes one or more bipolar electrodes that are configured to connect to a source of radio frequency energy. The vacuum line is configured to connect to a vacuum source and to draw moisture away from the one or more bipolar electrodes during tissue ablation. The controller is electrically coupled to the electrode carrier and configured to control the delivery of radio frequency energy to the one or more bipolar electrodes, such that tissue in contact with the electrode carrier can be ablated to a desired depth of destruction to achieve substantial hemostasis.

In general, in another aspect, the invention features a system for substantially achieving hemostasis by tissue ablation. The system includes a hemostasis device, a source of radio frequency, a controller and a vacuum source. The hemostasis device includes a base member, an electrode carrier and a vacuum line. The electrode carrier is attached to a surface of the base member and includes one or more bipolar electrodes. The one or more bipolar electrodes are configured to connect to the source of radio frequency energy. The vacuum line is configured to connect to the vacuum source. The source of radio frequency energy is electrically coupled to the one or more bipolar electrodes. The controller is configured to control the delivery of radio frequency energy from the source of radio frequency energy to the one or more bipolar electrodes, such that tissue can be ablated to a desired depth of destruction to achieve substantial hemostasis. The vacuum source is coupled to the vacuum line and operable to draw bleeding tissue into contact with the electrode carrier and to draw moisture generated during delivery of radio frequency energy to the one or more bipolar electrodes and ablation of the tissue away from the one or more bipolar electrodes, and to substantially eliminate liquid surrounding the one or more bipolar electrodes.

Implementations of the system or apparatus can include one or more of the following features. The apparatus can further include a porous layer positioned between the base member and the electrode carrier, the porous layer coupled to the vacuum line. The base member and the electrode carrier attached thereto can be substantially flexible, alternatively, the base member can be substantially rigid. In one embodiment, the base member is a glove including a palm region and finger regions and the electrode carrier is attached to the palm region of the base member. The glove can include one or more additional electrode carriers attached to the finger regions.

The electrode carrier can include woven strips of a non-conductive material, where the one or more bipolar electrodes include electrode wires woven in a first direction between the strips of non-conductive material. In one embodiment, sets of two or more electrode wires are woven in a first direction between each strip of non-conductive material orientated in the first direction, where each set of electrode wires alternates polarity, and a pair of sets of electrode wires comprises a bipolar electrode. The base member can be substantially cylindrically shaped, and the electrode carrier attached to an exterior surface of the cylindrically shaped base member. A second electrode carrier can be attached to an interior surface of the cylindrically shaped base member.

In general, in another aspect, the invention features a method for blood coagulation. An electrode carrier of a hemostasis device is positioned in contact with bleeding tissue. The hemostasis device includes a base member, the electrode carrier attached to a surface of the base member, the electrode carrier including one or more bipolar electrodes connected to a source of radio frequency energy, and a vacuum line connected to a vacuum source. A vacuum source is activated to draw the bleeding tissue into closer contact with the electrode carrier and to draw moisture released from the tissue during ablation away from the one or more bipolar electrodes. The source of radio frequency energy is activated and radio frequency energy is delivered to the one or more bipolar electrodes and ablates the tissue in contact with the one or more bipolar electrodes. The delivery of the radio frequency energy is ceased upon reaching a desired depth of destruction of the tissue. Hemostasis is substantially achieved in a region of the ablation.

In general, in another aspect, the invention features an apparatus for achieving hemostasis by tissue ablation including a base member shaped as a glove configured to be worn by a user. The apparatus further includes an electrode carrier attached to a surface of the base member and a controller. The electrode carrier includes one or more bipolar electrodes that are configured to connect to a source of radio frequency energy. The controller is electrically coupled to the electrode carrier and configured to control the delivery of radio frequency energy to the one or more bipolar electrodes, such that tissue in contact with the electrode carrier can be ablated to a desired depth of destruction to achieve substantial hemostasis.

Implementations of the apparatus can include one or more of the following. A porous layer can be positioned between the base member and the electrode carrier, the porous layer including a vacuum line configured to connect to a vacuum source and to draw moisture away from the one or more bipolar electrodes during tissue ablation. The base member can include a palm region and finger regions and the electrode carrier can be attached to the palm region of the base member. The apparatus can include one or more additional electrode carriers attached to undersides of the finger regions of the base member. The base member can include a main region corresponding to the hand of a glove and finger regions corresponding to fingers of a glove where the electrode carrier is attached to a top side of the main region opposite to a palm side of the main region. One or more additional electrode carriers can be attached to top sides of the finger regions of the base member.

The electrode carrier or carriers can include woven strips of a non-conductive material, where the one or more bipolar electrodes include electrode wires woven in a first direction between the strips of non-conductive material. In another embodiment, sets of two or more electrode wires are woven in a first direction between each strip of non-conductive material orientated in the first direction, where each set of electrode wires alternates polarity, and a pair of sets of electrode wires is a bipolar electrode.

Implementations of the invention can realize one or more of the following advantages. Hemostasis, the stoppage of bleeding, can be achieved quickly and in difficult to access locations in a patient's body. The hemostasis device can be used in trauma situations, such as the battleground, accident scenes or an emergency room, to quickly control bleeding and prevent the patient from bleeding to death. Tissue types that can bleed profusely and are difficult treat can be treated using the hemostasis device. The liver is a good example, as bleeding from the liver can be difficult to control, even under operating room conditions. The hemostasis device can have different configurations that are suited to different applications, for example, the device can be flexible, rigid, shaped as a glove, shaped cylindrically, etc. The depth of destruction of the tissue can be controlled so as to desiccate and coagulate the superficial tissue, without causing additional or unnecessary injury. The electrode carrier on the hemostasis device can be removed without restarting the bleeding, nor does pressure need to be applied after desiccation is complete.

The details of one or more embodiments of the invention are set forth in the accompanying drawings and the description below. Other features, objects, and advantages of the invention will be apparent from the description and drawings, and from the claims.

DESCRIPTION OF DRAWINGS

Like reference symbols in the various drawings indicate like elements.

DETAILED DESCRIPTION

A method and system for achieving hemostasis (the stoppage of bleeding) is described. RF (radio frequency) energy is used to ablate the surface of tissue to stop bleeding. The depth of destruction of the tissue can be controlled so as to desiccate and coagulate the superficial tissue, without causing additional or unnecessary injury. An electrode carrier including bipolar electrodes can be applied to the tissue, and RF energy transmitted through the bipolar electrodes to ablate the tissue. A layer of desiccated tissue, e.g., approximately 1 mm thick, can be created as well as coagulation of the tissue to achieve hemostasis. The electrode carrier can be removed without restarting the bleeding, nor does pressure need to be applied after desiccation is complete.

Figure 1A:
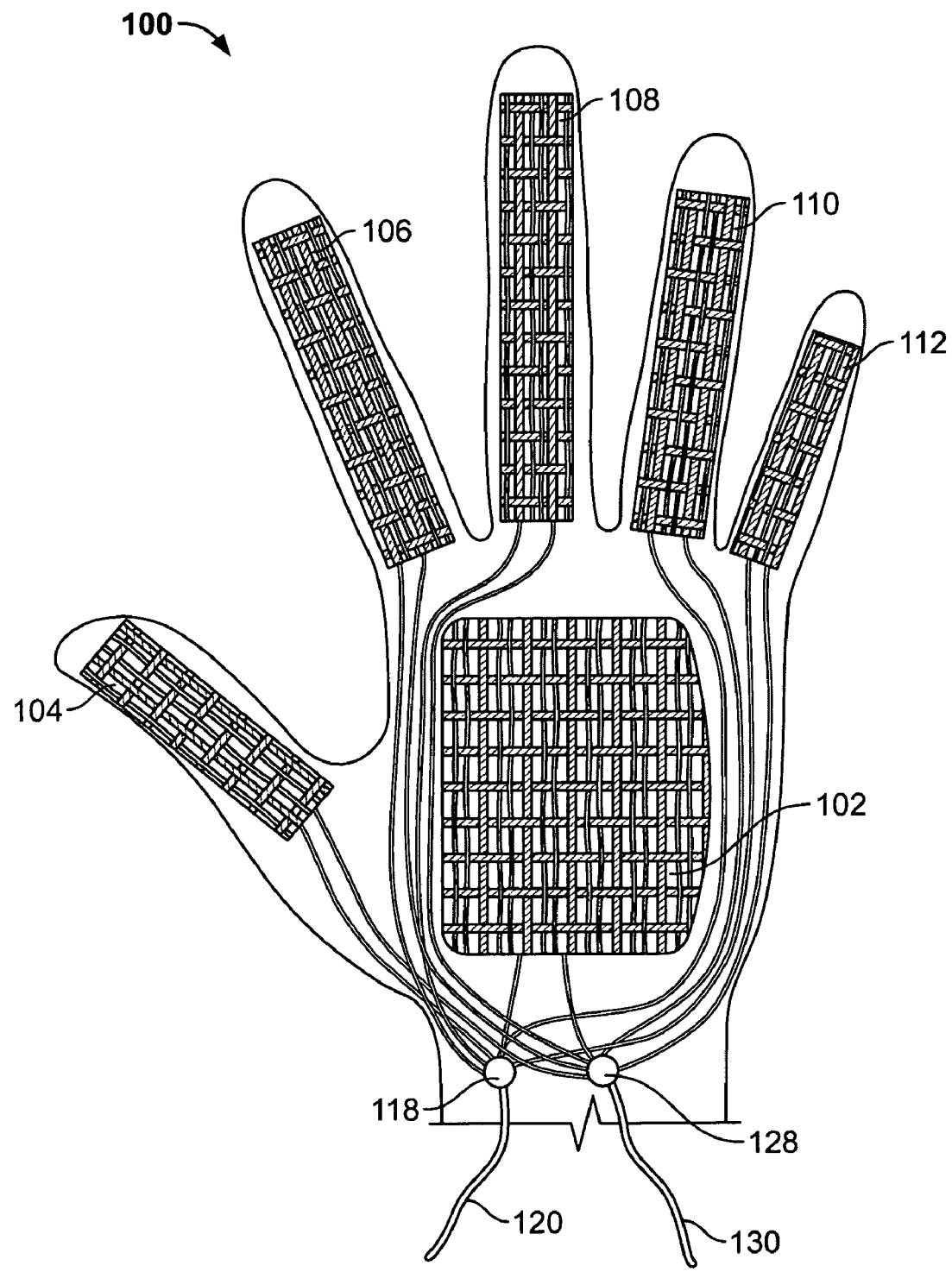
FIG. 1A is a schematic representation of a hemostasis device.

Referring to FIG. 1A, one embodiment of a hemostasis device 100 is shown. The base member of the hemostasis device 100 is configured as a glove and includes one or more electrode carriers. In the embodiment shown, a first electrode carrier 102 is included in the palm of the glove shaped hemostasis device 100, and five narrower electrode carriers 104-112 are included on the fingers and thumb of the hemostasis device 100. The glove-shaped hemostasis device 100 can fit over a user's hand, and is flexible so that the fingers can be extended or curled, etc., as desired by the user. The electrode carriers can have different configurations, e.g., the electrodes can extend along the proximal and/or distal ends of the palm and/or fingers.

Figure 1B:
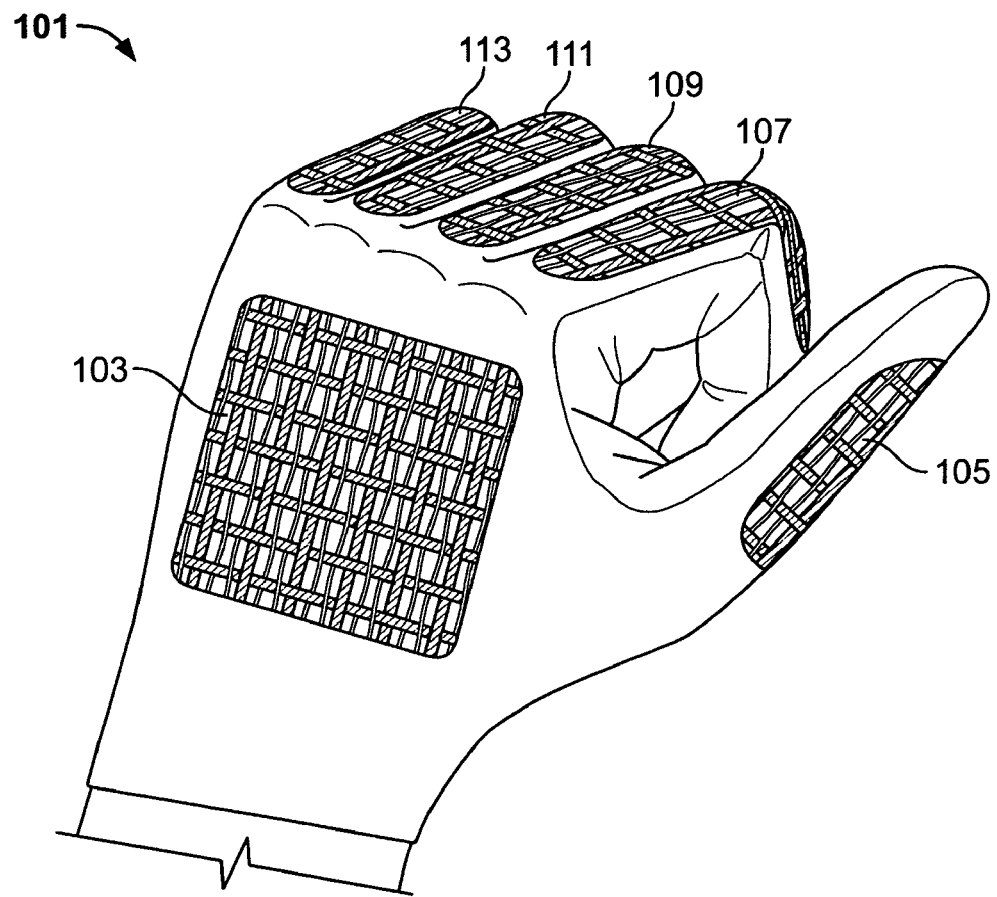
FIG. 1B is a schematic representation of an alternative embodiment of the hemostasis device of FIG. 1A.

Referring to FIG. 1B, in another embodiment of the hemostasis device 101, the electrode carriers are on the exterior surface of the glove shaped device, i.e., on the "top side" of the hand rather than on the "palm side". In the embodiment shown, a first electrode carrier 103 is included on the top of the glove shaped hemostasis device 101, and five narrower electrode carriers 105-113 are including on the tops of the fingers and thumb. In one application, a user can position the hemostasis device 101 within a cavity, e.g., a uterus, and form a fist to achieve hemostasis of the tissue within the cavity. In yet another embodiment, electrode carriers can be included on both the palm side and top side of the glove shaped device, or can be included on the fingers only or the palm and top of the hand only. Other configurations are possible.

Figure 2:
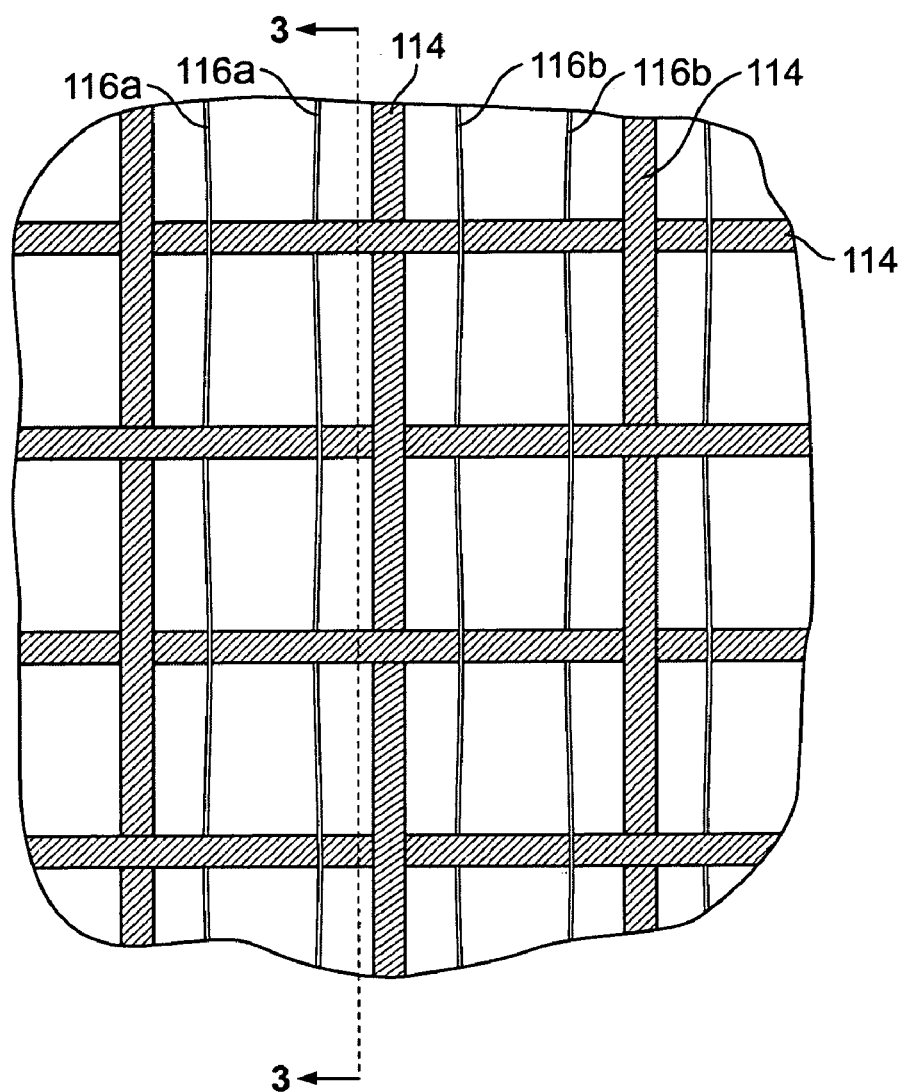
FIG. 2 is an enlarged view of a portion of an electrode carrier.

Referring again to FIG. 1A and to FIG. 2, an enlarged view is shown of a portion of the first electrode carrier 102. The electrode carrier 102 is formed from a woven insulative base material 114, which in one embodiment can be thin, plastic strips. Woven between the strips of base material 114 are electrodes 116. In this embodiment, the electrodes 116 are gold plated copper wires and two electrodes 116 are woven between each strip of base material 114. The electrodes 116 can be oppositely charged between each strip of base material 114. That is, electrodes 116a can be positively charged, and electrodes 116b can be negatively charged, with the strip of base material 114 providing a non-conductive region between the bi-polar electrode regions 116a, 116b. In another embodiment, a single electrode 116 can be woven between each strip of base material 114, with each electrode 116 alternating conductivity. In yet another embodiment, more than two electrodes 116 can be woven between each strip of base material. A pair of oppositely charged electrodes (or a pair of sets of electrodes) is referred to herein as a "bipolar electrode". Referring again to FIG. 1A, the electrodes 116 are electrically coupled to a connector 118 that can be electrically coupled by a cable 120 to an RF generator.

Figure 3:
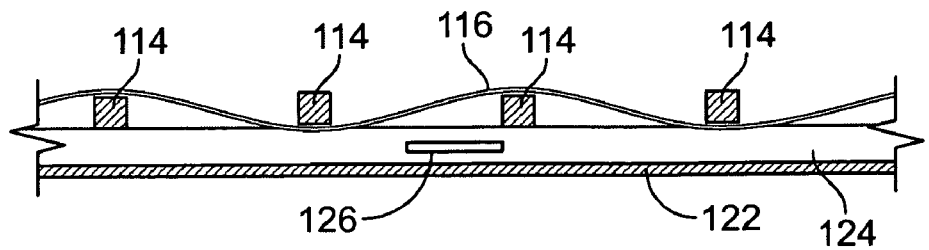
FIG. 3 is an enlarged cross-sectional view of a portion of an electrode carrier.

Referring to FIG. 3, a cross-sectional view is shown of the portion of the first electrode carrier 102 shown in FIG. 2 taken along line 3-3. The body 122 of the glove shaped hemostasis device 100 can be formed from a relatively thin and flexible material, e.g., nylon. As part of the body 122, or as a separate layer, a thermally insulating layer is included to protect the user's hand from temperatures generated during use of the hemostasis device 100 (e.g., from steam created from tissue desiccation). The electrode carrier 102 includes a porous layer 124 between the body 122 of the glove and the strips of base material 114 and electrodes 116. A vacuum line 126 is included within or under the porous layer 124 and is coupled to a vacuum port 128 that can be connected by a fluid line 130 to a vacuum source (FIG. 1). The porous layer 124 is configured such that when vacuum is applied through the vacuum line 126, tissue can be drawn into contact with the electrode carrier 102; the porous layer 124 facilitates spreading the vacuum over the surface of the electrode carrier 102. In one embodiment, the porous layer 124 can be formed from nylon and/or spandex. An electrode 116 is shown woven between the strips of base material 114.

Figure 4:
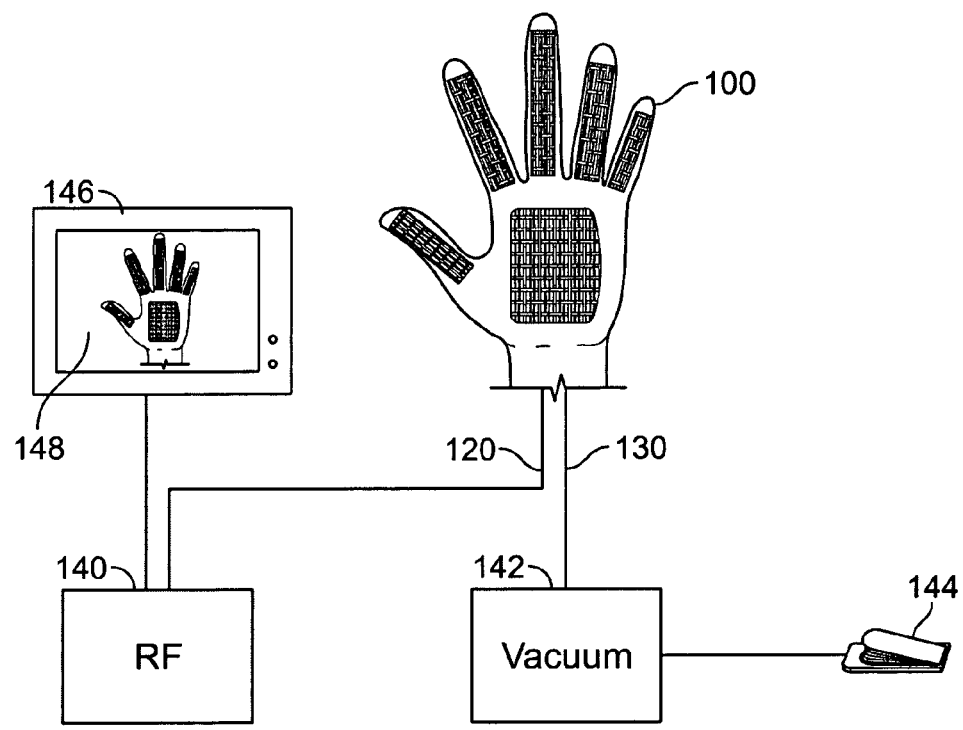
FIG. 4 is a schematic representation of a system including a hemostasis device.

Referring to FIG. 4, a system is shown including the hemostasis device 100, an RF generator 140 and a vacuum source 142. The RF generator 140 is coupled to the hemostasis device 100 by the cable 120. The vacuum source 142 is coupled to the hemostasis device 100 by the fluid line 130. In one embodiment, as shown, the vacuum source 142 can be activated by a foot pedal 144, to allow an operator of the hemostasis device 100 to keep both hands free to work with the bleeding tissue. In another embodiment, the RF generator 140 and the vacuum source 142 are combined into a single RF controller unit, which includes the RF generator, vacuum source, a vacuum monitoring system as well as a foot pedal 144 for activating both the RF energy and the vacuum. Additionally, a user input device including a display (e.g., similar to user input device 146 shown) can be included in the single RF controller unit.

In one embodiment, an operator can control which electrode carriers 102-112 are activated when using the hemostasis device 100. That is, for a particular application, using the palm electrode carrier 102 alone may be desirable. In an alterative application, for example, where a finger electrode carrier 106 can be placed over a cut in damaged tissue, it may be desirable to only activate the finger electrode carrier 106, so as not to unnecessarily ablate healthy (i.e., undamaged) tissue in contact with other parts of the hemostasis device 100. The RF generator 140 can be connected to a user input device 146 to receive instructions from a user as to which electrode carriers to activate.

In the embodiment shown, the user input device 146 includes a touch screen display 148. A visual representation of the hemostasis device 100 is shown on the touch screen display 148. Each electrode carrier on the hemostasis device 100 is represented by a corresponding graphic representation on the touch screen display 148. Once touched, the electrode carrier graphic becomes highlighted, indicating it has been selected, and by touching the graphic a second time, the electrode carrier is deselected. For example, by touching an area of the touch screen display 148 representing the palm electrode carrier 102, the RF generator, when activated (e.g., by depressing a foot pedal 144), is instructed to transmit RF energy to the palm electrode carrier 102.

In one implementation, routing the RF energy in this manner can be accomplished by having separate electrical connections, or pins, from the RF generator to each electrode carrier. Selecting a certain electrode carrier on the touch screen display 148 instructs the RF generator to close the switch to the pin of the corresponding electrode carrier on the hemostasis device 100. In this manner, once RF energy is initiated, the RF energy flows to only those electrode carriers that have been selected on the touch screen display 148. The user can select to activate some or all of the six electrode carriers 102-112. In one embodiment, conventional touch screen technology can be used to implement the touch screen display 148. Other types of user input devices 146 can be used, and the touch screen display 148 is just one example.

Figure 5:
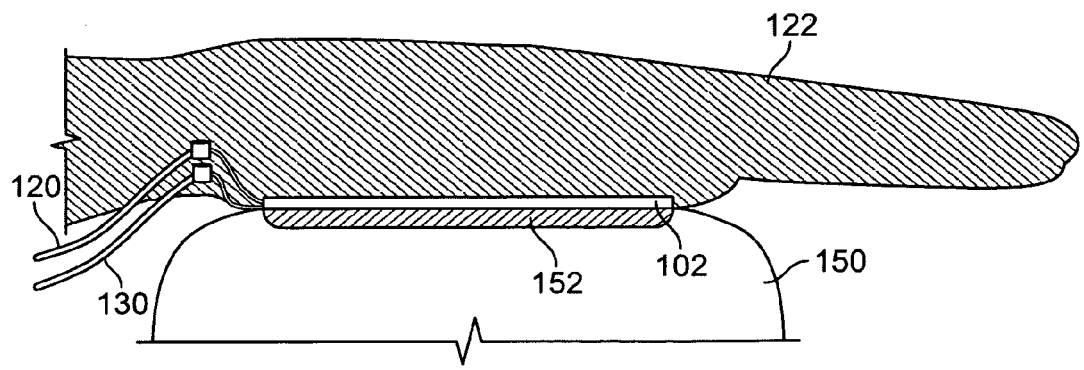
FIG. 5 is a side view of a portion of a hemostasis device in contact with tissue.
Figure 6:
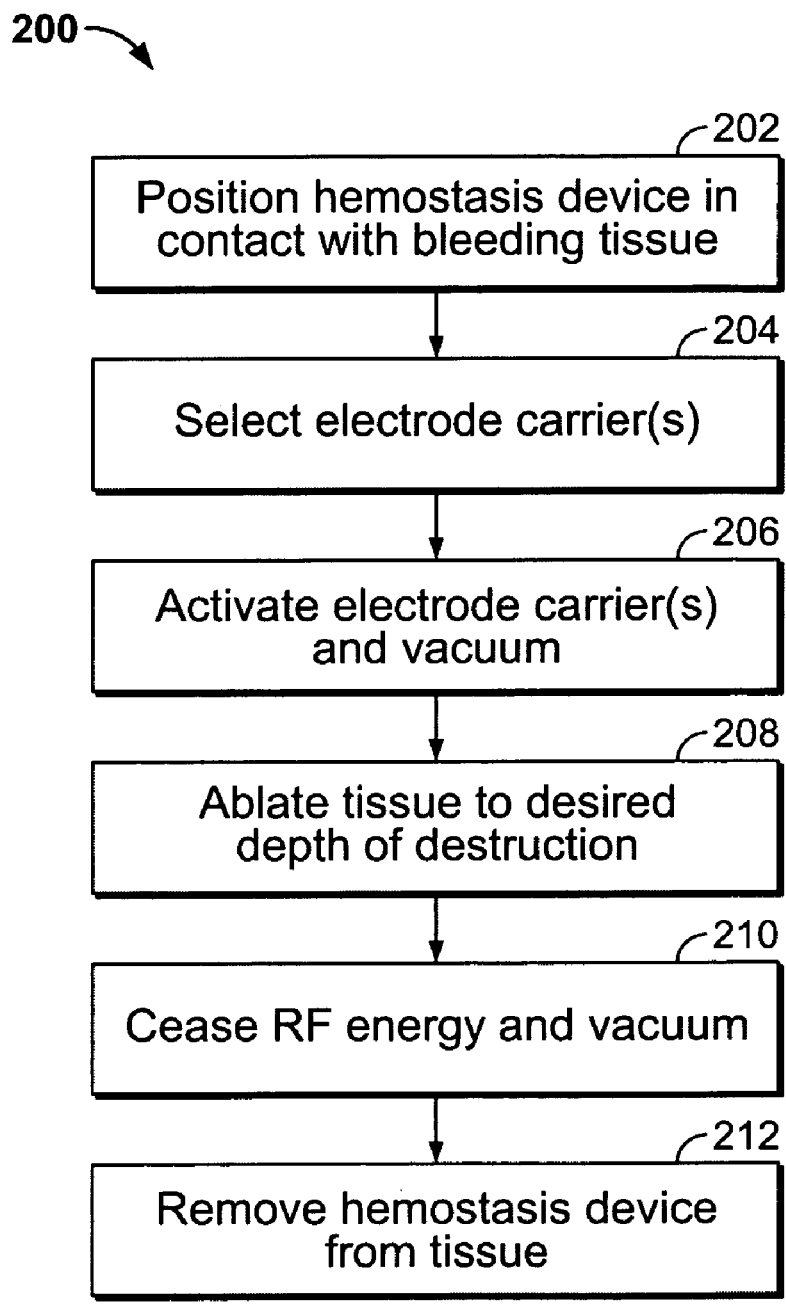
FIG. 6 is a flowchart showing a process for coagulating blood using a hemostasis device.

FIG. 5 shows a side view of the hemostasis device 100 in contact with damaged tissue 150. Referring to FIG. 6, a process 200 for using the hemostasis device 100 to stop bleeding from the damaged tissue 150 shall be described for illustrative purposes. The hemostasis device 100 is first positioned by the user in contact with the damaged tissue 150 (step 202). The user can exercise his/her discretion as to how the hemostasis device 100 is positioned, depending on the configuration of the tissue 150 to be treated. For example, the electrode carriers to be activated can be selected by the user or an assistant selectively touching the corresponding areas on the touch screen display 148 (step 204). The vacuum source 142 is activated, e.g., by depressing foot pedal 144 (step 206), causing the damaged tissue 150 to be drawn into closer contact with the hemostasis device 100, and simultaneous evacuation of blood, vapors and/or other material. The RF generator 140 receives the input from the user input device 146 and transmits RF energy to the selected electrode carrier 102 (step 206).

The damaged tissue 150 is ablated in the area in contact with the electrode carrier 102 until a desired depth of destruction is reached (step 208). The region 152 depicted in FIG. 5 represents the desiccated tissue. The RF energy and vacuum are ceased (step 210) and the hemostasis device 100 can be removed from the tissue 150 (step 212). Ablating the upper surface of the bleeding tissue, e.g., to a depth of approximately 1 to 7 mm, depending upon the type of tissue treated, desiccates and coagulates the tissue and achieves hemostasis. Because the bleeding has ceased due to desiccation of the tissue, rather than due to the application of pressure, the hemostasis device can be removed without restarting the bleeding. Optionally, a non-stick coating can be applied to the surface of the hemostasis device 100 to promote separation from the tissue after hemostasis is achieved and the procedure is complete.

To achieve the desired depth of ablation, a controller included in the RF generator 140 can monitor the impedance of the tissue at the electrodes 116 and include an automatic shut-off once a threshold impedance is detected. As the tissue 150 is desiccated by the RF energy, fluid is lost and withdrawn from the region by the vacuum 140 into the porous layer 124 and removed through the vacuum line 126. The vacuum draws moisture released by the tissue undergoing ablation away from the electrode carrier 102 and prevents formation of a low-impedance liquid layer around the electrodes 116 during ablation. As more of the tissue is desiccated, the higher the impedance experienced at the electrodes 116. By calibrating the RF generator 140, taking into account system impedance (e.g., inductance in cabling, etc.) and electrode carrier configuration (e.g., center-to-center distance between electrodes 116), a threshold impedance level can be set that corresponds to a desired depth of ablation. Once the threshold impedance is detected, the controller shuts off the RF energy, controlling the depth of tissue destruction. In an alternative embodiment, the RF generator 140 can be designed such that above the threshold impedance level the RF generator's ability to deliver RF energy is greatly reduced, which in effect automatically terminates energy delivery.

The depth of destruction is a function of a number of factors, including the tissue impedance, center-to-center distance between the positive and negative electrodes of a bipolar electrode and the surface density of the electrodes, as described further below. In one implementation, the user input device 146 can be configured to permit a user to select the depth of destruction, for example, by selecting the surface density of electrodes and/or center-to-center distance between the electrodes.

As described above in reference to FIG. 2, more or fewer electrodes 116 can be woven between each strip of base material 114, thereby increasing the surface density of the electrodes 116. If greater ablation depth is desired, more electrodes 116, e.g., five, can be woven between each strip of base material 114. Additionally, increasing the center-to-center distance between the positive electrode and negative electrode of a bipolar electrode can increase the depth of destruction. In the present example, a first set of five electrodes 116 can be positively energized and the adjacent set of five electrodes 116 negatively energized, which pattern is repeated across the electrode carrier 102. The entire grouping of 10 electrodes, i.e., the 5 positive and 5 negative electrodes, together are one bipolar electrode. The center-to-center distance between the set of positive electrodes and set of negative electrodes is thereby increased, which can increase the depth of ablation.

Figure 7A:
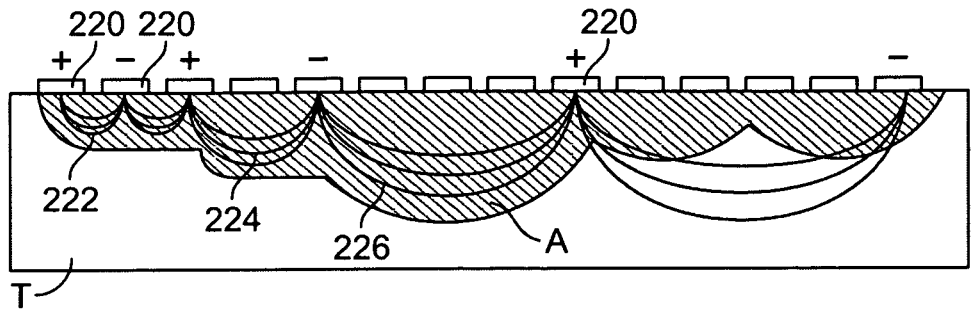
FIGS. 7A-D are schematic representations of cross-sectional views showing electrodes in contact with tissue for ablation.

Referring to FIG. 7A, preferably each electrode is energized at a polarity opposite from that of its neighboring electrodes. By doing so, energy field patterns, designated 222, 224 and 226 in FIG. 7A, are generated between the electrode sites and thus help to direct the flow of current through the tissue T to form a region of ablation A. As can be seen in FIG. 7A, if electrode spacing is increased by energizing, for example, every third or fifth electrode 220 rather than all electrodes, the energy patterns will extend more deeply into the tissue. See, for example, pattern 224 which results from energization of electrodes having a non-energized electrode between them, or pattern 226 which results from energization of electrodes having two non-energized electrodes between them.

The depth of ablation is also effected by the electrode density (i.e., the percentage of the target tissue area which is in contact with active electrode surfaces) and may be regulated by pre-selecting the amount of this active electrode coverage. For example, the depth of ablation is much greater when the active electrode surface covers more than 10% of the target tissue than it is when the active electrode surfaces covers only 1% of the target tissue.

By way of illustration, by using 3-6 mm spacing and an electrode width of approximately 0.5-2.5 mm, delivery of approximately 20-40 watts over a 9-16 cm² target tissue area will cause ablation to a depth of approximately 5-7 millimeters when the active electrode surface covers more than 10% of the target tissue area. After reaching this ablation depth, the impedance of the tissue will become so great that ablation will self-terminate. By contrast, using the same power, spacing, electrode width, and RF frequency will produce an ablation depth of only 2-3 mm when the active electrode surfaces covers less than 1% of the target tissue area. This can be better understood with reference to FIG. 7B, in which high surface density electrodes are designated 220A and low surface density electrodes are designated 220B. For purposes of this comparison between low and high surface density electrodes, each bracketed group of low density electrodes is considered to be a single electrode. Thus, the electrode widths W and spacings S extend as shown in FIG. 7B.

Figure 7B:
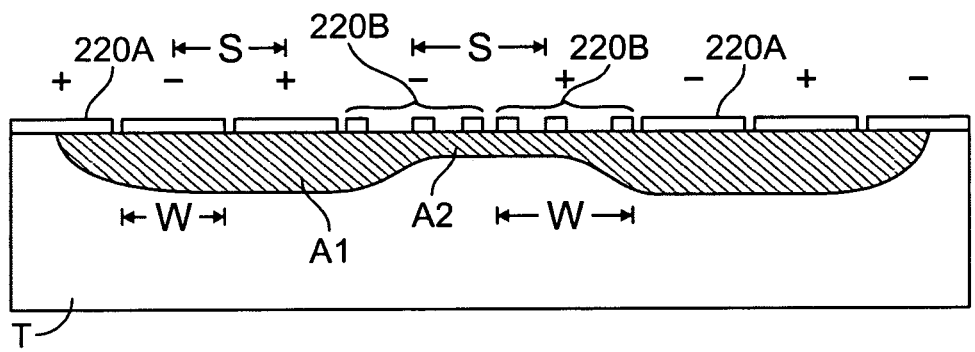

As is apparent from FIG. 7B, the electrodes 220A, which have more active area in contact with the underlying tissue T, produce a region of ablation A1 that extends more deeply into the tissue T than the ablation region A2 produced by the low density electrodes 220B, even though the electrode spacings and widths are the same for the high and low density electrodes. Some examples of electrode widths, having spacings with more than 10% active electrode surface coverage, and their resultant ablation depth, based on an ablation area of 6 cm² and a power of 20-40 watts, are given on the following table:

| ELECTRODE WIDTH | SPACING | APPROX. DEPTH |
|---|---|---|
| 1 mm | 1-2 mm | 1-3 mm |
| 1-2.5 mm | 3-6 mm | 5-7 mm |
| 1-4.5 mm | 8-10 mm | 8-10 mm |

Examples of electrode widths, having spacings with less than 1% active electrode surface coverage, and their resultant ablation depth, based on an ablation area of 6 cm² and a power of 20-40 watts, are given on the following table:

| ELECTRODE WIDTH | SPACING | APPROX. DEPTH |
|---|---|---|
| 1 mm | 1-2 mm | 0.5-1 mm |
| 1-2.5 mm | 3-6 mm | 2-3 mm |
| 1-4.5 mm | 8-10 mm | 2-3 mm |

Thus it can be seen that the depth of ablation is significantly less when the active electrode surface coverage is decreased.

Figure 7C:
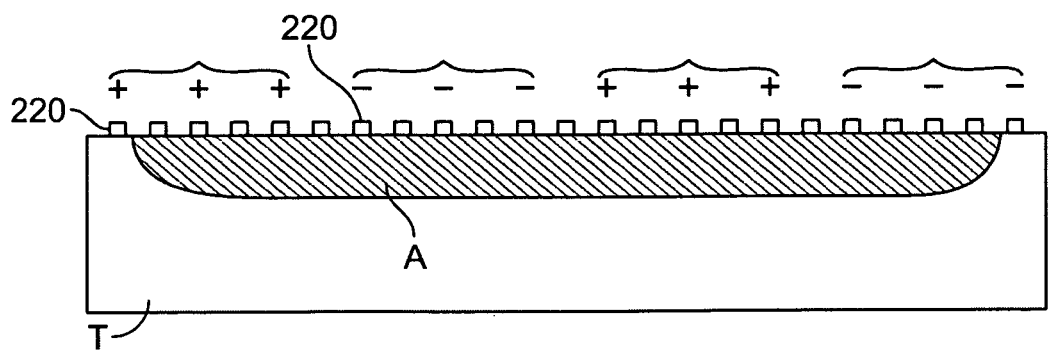
Figure 7D:
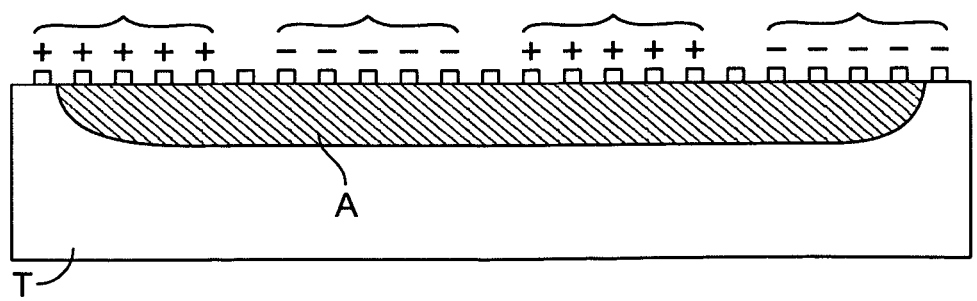

Referring to FIG. 7C, if multiple, closely spaced, electrodes 220 are provided on the electrode carrying member, a user may set the RF generator 140 to energize electrodes which will produce a desired electrode spacing and active electrode area. For example, alternate electrodes may be energized as shown in FIG. 7C, with the first three energized electrodes having positive polarity, the second three having negative polarity, etc. All six electrodes together can be referred to as one bipolar electrode. As another example, shown in FIG. 7D, if greater ablation depth is desired the first five electrodes may be positively energized, and the seventh through eleventh electrodes negatively energized, with the sixth electrode remaining inactivated to provide adequate electrode spacing. A user can therefore not only control which electrode carriers are activated, but in one implementation can also control which electrodes are energized within an electrode carrier to produce a desired depth of destruction.

Figure 8:
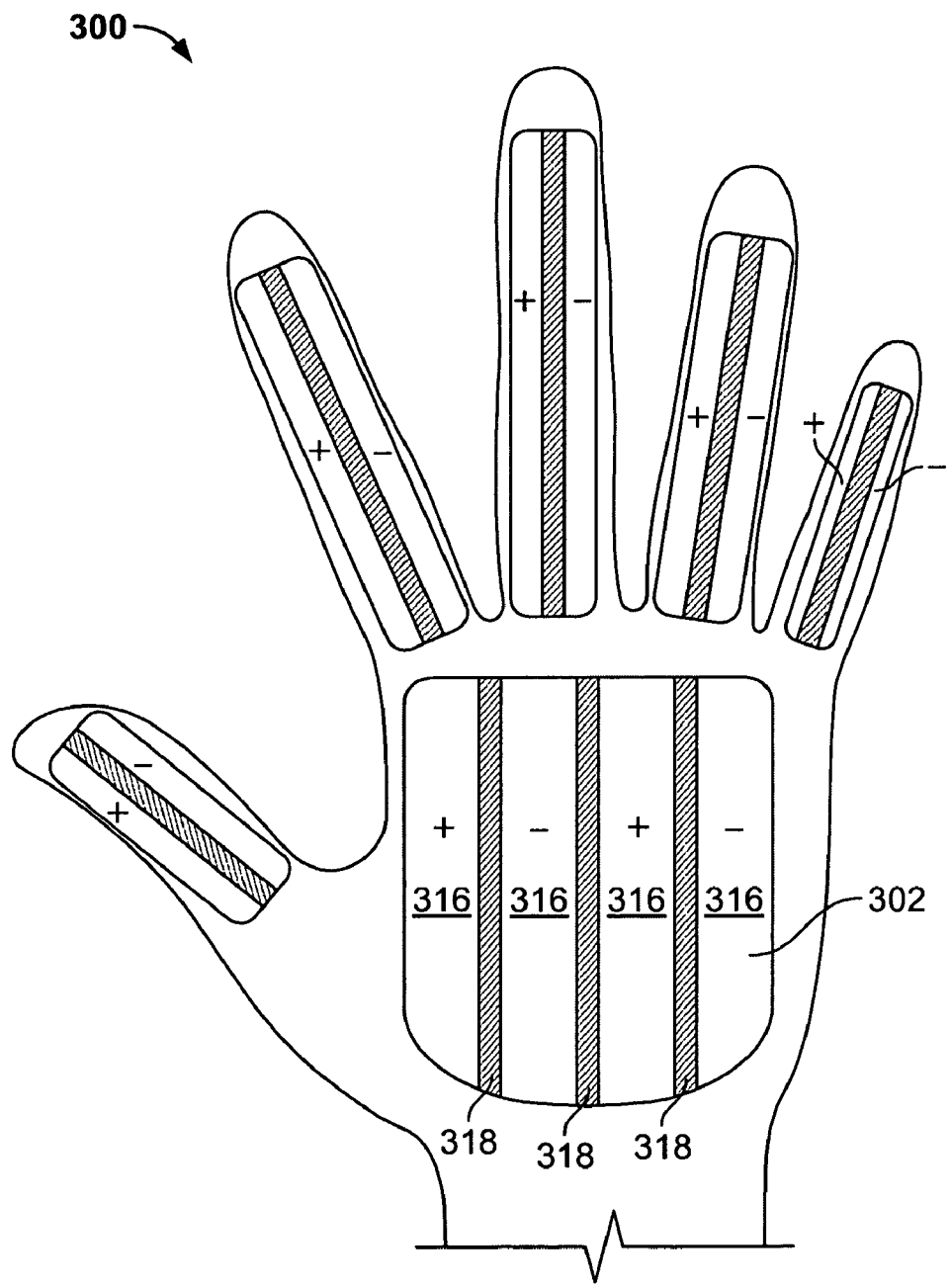
FIG. 8 is a schematic representation of an alternative embodiment of a hemostasis device.

Other embodiments of the one or more electrode carriers are possible. For example, referring to FIG. 8, in one embodiment, an electrode carrier, e.g., the palm electrode carrier 302, can be formed of a fabric that is metallized in regions to form the electrodes 316. The electrodes 316 are conductive and alternate between positive and negative polarity. Non-conductive insulator regions 318 separate the electrodes 316. For example, the fabric can be a composite yarn with a thermoplastic elastomer (TPE) core and multiple polyfilament nylon bundles wound around the TPE as a cover. The nylon bundles are plated with thin, conductive metal layers. This construction is flexible, and can facilitate achieving close contact between the electrode carrier 302 and an irregularly shaped area of tissue. Other configurations for the electrode carriers 102-112 are possible, and the above described embodiments are merely exemplary electrode carriers.

Figure 9:
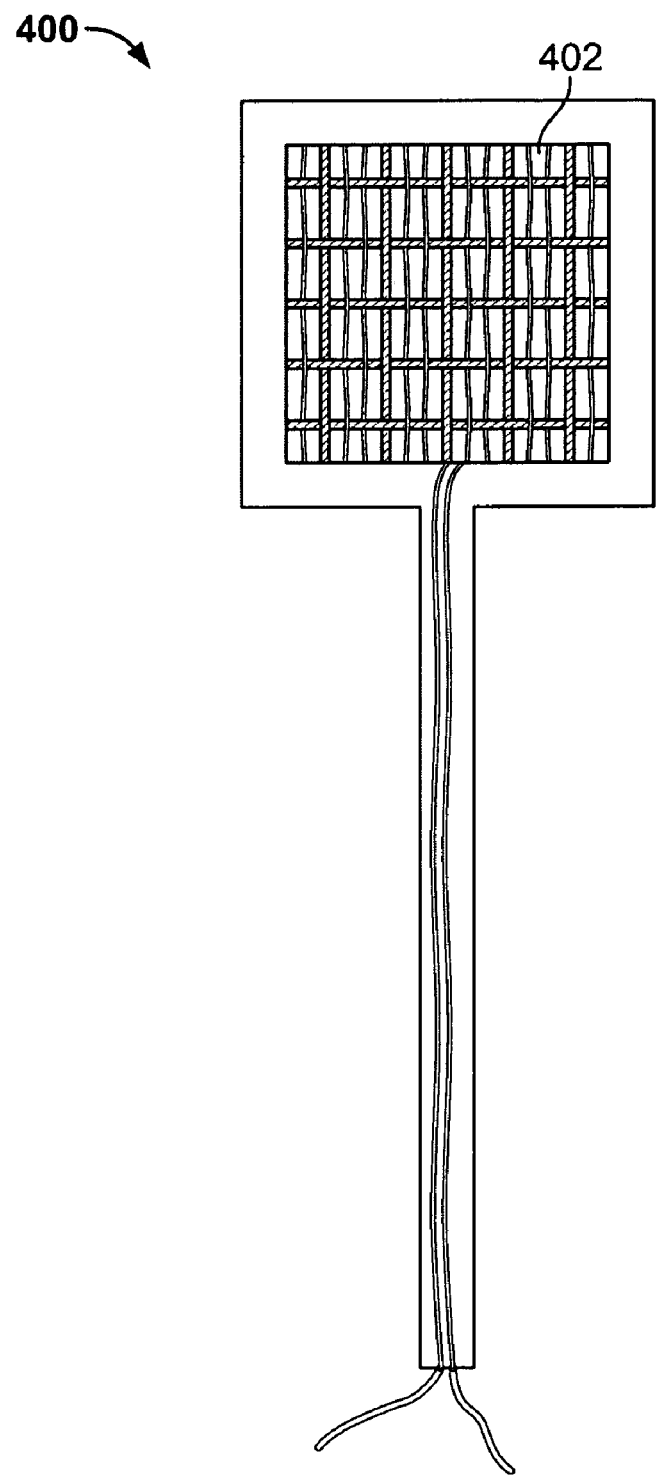
FIG. 9 is a schematic representation of another alternative embodiment of a hemostasis device.

The hemostasis device has been described with reference to an embodiment where the electrode carrier or carriers are on the surface of a glove that can be worn by a user. Other embodiments of the base member of the hemostasis device are possible. For example, referring to FIG. 9, in one embodiment the base member 400 can be a paddle with a handle. One or more electrode carriers 402 can be affixed to the surface of the paddle 400, which can be manipulated by a user into a position in contact with damaged tissue. A porous layer is included beneath the electrode carrier 402 and a vacuum source can be connected to a vacuum line within or under the porous layer to provide vacuum at the electrode carrier surface, as described above in reference to the glove-shaped embodiment.

In one embodiment, the paddle 400 can be formed smaller than a human hand, such that the paddle 400 can reach into areas that might otherwise be inaccessible by a human hand if using the glove-configured hemostasis device 100. In another embodiment, the paddle 400 and electrode carrier 402 can be formed larger than the palm of a human hand, such that the electrode carrier 402 can be used to cover relatively large areas of damaged tissue, i.e., larger than can be covered by the palm electrode carrier 102 of the glove-configured hemostasis device 100. Other configurations of the hemostasis device are possible, including different shapes and sizes. The paddle 400, or otherwise configured base member, can be flexible so as to conform to the surface of damaged tissue, or can be substantially rigid, which may be desirable in certain applications.

The hemostasis device can be used to achieve hemostasis under urgent, life-threatening conditions, e.g., on a battlefield or at the scene of an accident, or under controlled conditions, e.g., during surgery. For example, a soldier suffering an injury to the liver on the battlefield is often at risk of bleeding to death within a considerably short period of time. The liver is an organ that once damaged can bleed profusely, and the surface is such that the liver cannot simply be sutured to stop bleeding. The hemostasis device, for example the glove-shaped hemostasis device 100, can be ideal in such situations. A user, even under battlefield conditions, can put on the glove-shaped hemostasis device 100, reach into the soldier's body, find the damaged liver, activate the desired one or more electrode carriers, and achieve hemostasis in a very short period of time. A soldier who may have otherwise bled to death could be saved using the hemostasis device 100.

The hemostasis device can also be useful in surgical procedures. By way of illustrative example, consider a liver that has been diagnosed as including a tumor that must be removed to save a patient's life. Using conventional techniques, to remove the tumor one or more incisions into the liver would be necessary. Cutting into the liver tissue typically triggers profuse bleeding that can be difficult to control, even under operating room conditions. The hemostasis device can instead be used to achieve almost immediate hemostasis, avoiding unnecessary blood loss from the patient. For example, after making an incision into the liver, a user wearing the glove-shaped hemostasis device 100 can lay a finger over the incision and activate the electrode carrier corresponding to the finger. RF energy transmitted to the activated electrode carrier can quickly achieve hemostasis.

Figure 10:
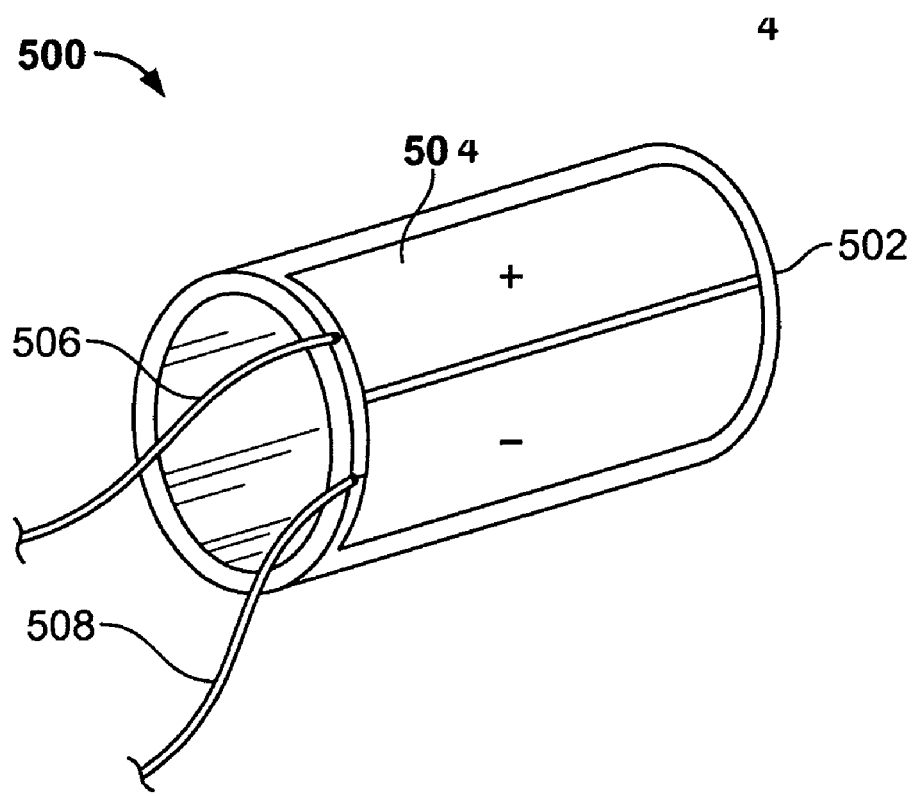
FIG. 10 is a schematic representation of a cylindrically shaped embodiment of a hemostasis device.

In an alternative implementation, the base member of the hemostasis device 500 can be cylindrically shaped as shown in FIG. 10. One or more bipolar electrodes 504 can be positioned on the exterior surface of the hemostasis device 500. A cable 508 can connect the one or more bipolar electrodes 504 to an RF energy source, and a fluid line 506 can connect a porous layer beneath the bipolar electrodes to a vacuum source. Optionally, a distal end 502 of the hemostasis device 500 can be sharpened so the hemostasis device 500 can cut into the tissue while being inserted into position. The hemostasis device 500 can be inserted into tissue, for example, a liver including a tumor, so that the tumor is within the interior of the hemostasis device 500 when it is positioned in the liver. The one or more bipolar electrodes 504 on the exterior of the hemostasis device 500 can be activated, and the surrounding tissue ablated. The hemostasis device 500 and the tissue within the interior core can be removed from the liver. The tumor is thereby extracted from the liver, and hemostasis in achieved in the surrounding tissue. In another embodiment, one or more bipolar electrodes can be included on the interior of the hemostasis device 500. Other configurations are possible.

Other embodiments of the base member and hemostasis device are possible, and the ones described above are merely exemplary. Additionally, other procedures for using the hemostasis device are possible, and the battlefield and surgical procedures described above were examples for illustrative purposes.

A number of embodiments of the invention have been described. Nevertheless, it will be understood that various modifications may be made without departing from the spirit and scope of the invention. Accordingly, other embodiments are within the scope of the following claims.

What is claimed is:

1. An apparatus for substantially achieving hemostasis by tissue ablation, comprising:
   a base member comprised of a porous layer;
   an electrode carrier attached to a surface of the base member, the electrode carrier including one or more bipolar electrodes that are configured to connect to a source of radio frequency energy;
   a vacuum line included within the porous layer of the base member and configured to connect to a vacuum source, wherein the porous layer is configured to enable the vacuum line to draw tissue towards the bipolar electrodes during tissue ablation; and
   a controller electrically coupled to the electrode carrier and configured to control the delivery of radio frequency energy to the one or more bipolar electrodes such that tissue in contact with the electrode carrier can be ablated to a desired depth of destruction to achieve substantial hemostasis.

2. The apparatus of claim 1, where the base member and the electrode carrier attached thereto are substantially flexible.

3. The apparatus of claim 2, where the base member comprises a glove including a palm region and finger regions and the electrode carrier is attached to the palm region of the base member.

4. The apparatus of claim 3, further comprising one or more additional electrode carriers, where the one or more additional electrode carriers are attached to the finger regions of the base member.

5. The apparatus of claim 1, where the electrode carrier comprises woven strips of a non-conductive material and where the one or more bipolar electrodes comprise electrode wires woven in a first direction between the strips of non-conductive material.

6. The apparatus of claim 5, where sets of two or more electrode wires are woven in a first direction between each strip of non-conductive material orientated in the first direction, where each set of electrode wires alternates polarity, and a pair of sets of electrode wires comprises a bipolar electrode.

7. The apparatus of claim 1, where the base member is substantially rigid.

8. A system for substantially achieving hemostasis by tissue ablation, comprising: a hemostasis device including:
   a base member comprised of a porous layer;

an electrode carrier attached to a surface of the base member, the electrode carrier including one or more bipolar electrodes, the one or more bipolar electrodes configured to connect to a source of radio frequency energy;

a vacuum line provided within the porous layer of the base member and configured to connect to a vacuum source, wherein the porous layer is configured to draw tissue towards the bipolar electrodes during tissue ablation;

a source of radio frequency energy electrically coupled to the one or more bipolar electrodes; and a controller to control the delivery of radio frequency energy from the source of radio frequency energy to the one or more bipolar electrodes such that tissue can be ablated to a desired depth of destruction to achieve substantial hemostasis.

9. The system of claim 8, where the hemostasis device further comprises: a thermally insulated layer for protecting a user of the hemostasis device from the electrode carrier.

10. The system of claim 8, further comprising: one or more additional electrode carriers; and a user input device configured to receive input from a user selecting one or more of the electrode carriers, the user input device coupled to the source of radio frequency energy; where the source of radio frequency energy is operable to deliver radio frequency energy to the one or more electrode carriers based on the user input.

11. The system of claim 8, where the base member and the electrode carrier of the hemostasis device are substantially flexible.

12. The system of claim 11, where the base member of the hemostasis device comprises a glove including a palm region and finger regions and the electrode carrier is attached to the palm region of the base member.

13. The system of claim 12, further comprising one or more additional electrode carriers, where the one or more additional electrode carriers are attached to the finger regions of the base member.

14. The system of claim 8, where the electrode carrier comprises woven strips of a non-conductive material and where the one or more bipolar electrodes comprise electrode wires woven in a first direction between the strips of non-conductive material.

15. The system of claim 14, where sets of two or more electrode wires are woven in a first direction between each strip of non-conductive material orientated in the first direction, where each set of electrode wires alternates polarity, and a pair of sets of electrode wires comprises a bipolar electrode.

16. The system of claim 8, where the base member is substantially rigid.

17. A method for blood coagulation, comprising:
positioning an electrode carrier of a hemostasis device in contact with bleeding tissue, the hemostasis device including:
a base member comprised of a porous layer, the electrode carrier attached to a first surface of the porous layer of the base member, the electrode carrier including one or more bipolar electrodes connected to a source of radio frequency energy, and a vacuum line included within the porous layer of the base member and coupled to a vacuum source;
activating the vacuum source to draw the bleeding tissue into closer contact with the porous layer and thereby the electrode carrier and to draw moisture released from the tissue during ablation away from the one or more bipolar electrodes;
activating the source of radio frequency energy and delivering radio frequency energy to the one or more bipolar electrodes and ablating the tissue in contact with the one or more bipolar electrodes; and
ceasing delivery of the radio frequency energy upon reaching a desired depth of destruction of the tissue; wherein hemostasis is substantially achieved in a region of the ablation.

18. The method of claim 17, where the porous layer is positioned between the base member and the electrode carrier and coupled to the vacuum line, where upon activating the vacuum source the porous layer facilitates distributing the vacuum across the electrode carrier.

19. An apparatus for achieving hemostasis by tissue ablation, comprising:
a base member shaped as a glove configured to be worn by a user and comprising a porous layer including a vacuum line couplable to a vacuum source to enable tissue to be drawn to the porous layer during ablation and an insulating layer for protecting the user during ablation;
an electrode carrier attached to the porous layer of the base member, the electrode carrier including one or more bipolar electrodes that are configured to connect to a source of radio frequency energy during ablation; and
a controller electrically coupled to the electrode carrier and configured to control the delivery of radio frequency energy to the one or more bipolar electrodes such that tissue in contact with the electrode carrier can be ablated to a desired depth of destruction to achieve substantial hemostasis.

20. The apparatus of claim 19, where the base member includes a palm region and finger regions and the electrode carrier is attached to the palm region of the base member.

21. The apparatus of claim 20, further comprising one or more additional electrode carriers, where the one or more additional electrode carriers are attached to undersides of the finger regions of the base member.

22. The apparatus of claim 19, where the base member includes a main region corresponding to the hand of a glove and finger regions corresponding to fingers of a glove and the electrode carrier is attached to a top side of the main region opposite to a palm side of the main region.

23. The apparatus of claim 22, further comprising one or more additional electrode carriers, where the one or more additional electrode carriers are attached to top sides of the finger regions of the base member.

24. The apparatus of claim 19, where the electrode carrier comprises woven strips of a non-conductive material and where the one or more bipolar electrodes comprise electrode wires woven in a first direction between the strips of non-conductive material.

25. The apparatus of claim 24, where sets of two or more electrode wires are woven in a first direction between each strip of non-conductive material orientated in the first direction, where each set of electrode wires alternates polarity, and a pair of sets of electrode wires comprises a bipolar electrode.

* * * * *